(12) United States Patent
Bluecher et al.

(10) Patent No.: US 11,942,878 B2
(45) Date of Patent: Mar. 26, 2024

(54) MICROSTRUCTURED FIELD EFFECT DEVICE

(71) Applicant: BVW Holding AG, Cham (CH)

(72) Inventors: Lukas Bluecher, Eurasburg (DE); Michael Milbocker, Holliston, MA (US)

(73) Assignee: BVW Holding AG, Cham (CH)

( * ) Notice: Subject to any disclaimer, the term of this patent is extended or adjusted under 35 U.S.C. 154(b) by 605 days.

(21) Appl. No.: 16/837,819

(22) Filed: Apr. 1, 2020

(65) Prior Publication Data

US 2021/0307891 A1    Oct. 7, 2021

(51) Int. Cl.
| | | |
|---|---|---|
| *H02N 13/00* | (2006.01) | |
| *A61F 2/02* | (2006.01) | |
| *A61F 2/00* | (2006.01) | |
| *A61F 2/48* | (2006.01) | |

(52) U.S. Cl.
CPC ............... *H02N 13/00* (2013.01); *A61F 2/02* (2013.01); *A61F 2002/0086* (2013.01); *A61F 2/482* (2021.08)

(58) Field of Classification Search
CPC . H02N 13/00; H01L 21/6833; H01L 21/6831; H01L 21/683
USPC .......................................................... 361/234
See application file for complete search history.

(56) References Cited

U.S. PATENT DOCUMENTS

| | | | |
|---|---|---|---|
| 9,120,670 B2 | 9/2015 | Hulseman et al. | |
| 9,908,274 B2 | 3/2018 | Hulseman et al. | |
| 9,988,201 B2 | 6/2018 | Darin et al. | |
| 10,377,044 B2 | 8/2019 | Hulseman et al. | |
| 10,458,053 B2 | 10/2019 | Hulseman et al. | |
| 10,575,667 B2 | 3/2020 | Hulseman et al. | |
| 10,687,642 B2 | 6/2020 | Hulseman et al. | |
| 10,889,005 B2 | 1/2021 | Hulseman et al. | |
| 2012/0034390 A1* | 2/2012 | Suh ....................... | B81C 1/0046 427/510 |
| 2012/0276334 A1* | 11/2012 | Fedynyshyn ............ | B05D 5/08 264/293 |
| 2015/0174768 A1* | 6/2015 | Rodnick ........... | H01L 21/67766 294/212 |

(Continued)

OTHER PUBLICATIONS

Temple, B., "The Effect of Bending Compliance on Adhesion Pressure of Hybrid Electrostatic/Gecko-like Adhesives", IEEE International Conference on Robotics and Automation (ICRA), May 21-25, 2018.

*Primary Examiner* — Danny Nguyen
(74) *Attorney, Agent, or Firm* — Patterson Intellectual Property Law, P.C.; Ryan D. Levy; Mark A. Kilgore

(57) ABSTRACT

A microstructured device is disclosed utilizing Coulomb field modification of surface energy and electroadhesion to localize a device surface or to levitate a device surface with respect to a target surface. The surface energy modification can be permanent or reversible depending on whether the charge is externally delivered to the device or derived on the device galvanically. The microstructure aspect of the device induces various hydrophilic/hydrophobic interactions with the target surface. The Coulomb field can be used to enhance or decrease the hydrophilic/hydrophobic interactions. In combination, the disclosed electro-microstructured device provides for localizing implants in a mammalian body, and additionally means for controlling cell interaction with the implant.

18 Claims, 11 Drawing Sheets

(56) References Cited

U.S. PATENT DOCUMENTS

| | | |
|---|---|---|
| 2015/0368838 A1 | 12/2015 | Hulseman et al. |
| 2017/0014111 A1 | 1/2017 | Hulseman et al. |
| 2019/0062155 A1 | 2/2019 | Hulseman et al. |
| 2019/0240845 A1* | 8/2019 | Hart ..................... B25J 15/0085 |
| 2020/0254718 A1* | 8/2020 | Kim ......................... B32B 7/12 |
| 2020/0338808 A1 | 10/2020 | Hulseman et al. |
| 2020/0346476 A1* | 11/2020 | Hart ........................ B41M 1/00 |
| 2021/0086371 A1 | 3/2021 | Hulseman et al. |
| 2021/0114101 A1* | 4/2021 | Lafarre ................... B05D 3/06 |

\* cited by examiner

MICROSTRUCTURED FIELD EFFECT DEVICE

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

This application claims benefit of the following patent application(s) which is/are hereby incorporated by reference: None

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND SUMMARY

This disclosure relates to microstructured devices that have an electrical management system that can alter the state of the microstructured device's physical characteristics. The disclosure also relates to microstructured surfaces that may interact with target surfaces through electroadhesion and electrowetting by changing the surface energy of the disclosed microstructured surface. Further, electroadhesive microstructured surfaces, both implantable and generic grip-enhancing surfaces, are disclosed herein.

It is known in the prior art that surfaces can undergo modification of the surface's wetting properties with an applied electric field, which is known as electrowetting. Electrowetting can be understood based on the forces that result from the applied electric field. Generally, electrowetting is utilized on hydrophobic surfaces. Normally, water will approximate a sphere when placed on a hydrophobic surface because the attraction between the water molecules counters the gravitational force which would tend to flatten the water on the surface. Conversely, a nonpolar liquid will possess little self-attraction, and hence nonpolar liquids may spread on a hydrophobic surface under the action of gravity. In comparison, when water is placed on a hydrophilic surface the tendency of the water to form a sphere through self-attraction is counterbalanced by the attraction of the water to the hydrophilic surface, hence gravity dominates, and the water drop spreads. When a nonpolar liquid is placed on a hydrophilic surface one might think gravity would predominate, but in some cases surface tension dominates, and nonpolar liquids will often form a spherical configuration on a hydrophobic surface.

Recently, exogenous electric fields have been found useful in modulating cellular function, e.g. cell migration in wound healing. There has been a steady increase in therapeutic devices and wound dressings utilizing the influence of static or dynamic electric fields, especially in the repair of bones. These devices use large electrodes, and macroscopically uniform electromagnetic fields.

However, the disclosures provided in this specification concern field strengths of magnitude on the order of a 100 kV/m field. If such a field were placed on large electrodes macroscopically spaced, typically this field strength is sufficient for large scale electroporation and electrofusion of tissue. In contrast, because the fields generated as described below in more detail are on a micrometer scale, they do not cause electroporation and electrofusion of tissue. Thus, high field gradient does not equate with high energy density on microscales.

Those who have experimented with electroadhesion understand that the forces actually generated are considerably lower than those calculated from theory. This departure from theory is due to the fact that no real substance is a perfectly homogeneous dielectric. This inhomogeneity inhibits electroadhesivity when the inhomogeneity is random. On the other hand, hierarchically structured inhomogeneity can enhance the prehension force above the theoretical expectation value. The microstructured dielectric in combination with microstructured charge localization can be used to geometrically control electroadhesive force. For example, the same device can both localize the device in living tissue and direct cell mobility with respect to the device.

Another departure from theory is the fact that the contact between dielectric and target object is never perfect. As described below, the microstructure of a surface can play an important role. It is a goal of this disclosure to describe the use of hierarchically microstructured surfaces which may significantly improve dielectric contact both through localized electric forces (high field gradient) and the formation of composite hydrophilic/hydrophobic domains known as Wenzel-Cassie interfaces.

It should be appreciated that an electroadhesive effect is an effect where the total energy of two surfaces when they are apart is greater than the total energy when the two surfaces are in contact. Conversely, an electrorepulsive effect is an effect where the total energy of two surface when they are apart is less than the total energy when the two surfaces are in contact. While this specification will use the word electroadhesion to describe adhering surfaces with high shear and peel forces, the opposite is also possible, i.e., surfaces with low shear and peel force.

These effects due to hierarchical arrangement of microscopic surface texture, both random and regular, create spatially resonant effects that reinforce and amplify relatively weak effects. In particular, spatial resonance can lead to interlocking regions of highly attractive and repulsive microscopic regions in an interface between a microstructured surface and a wide variety of target surfaces.

These interlocking regions of attractive and repulsive microscopic regions cause an engineered surface to be strongly adherent to a surface, without causing frictional or abrasive damage to the target surface. Engineered surfaces of this type are of particular value in the surgical suite, where manipulation of tissue can cause frictional or abrasive tissue damage and cause post-surgical adhesions. Commonly, this frictional tissue damage is not observable by the unaided eye and is frequently discounted. Hence many of the beneficial aspects and hence the applications of the microstructured electroadhesive devices of the present specification are not yet appreciated or anticipated.

BRIEF SUMMARY

The current disclosure provides in one embodiment an electro-microstructured device which may include a microstructure surface and at least one electrode. The microstructured device may include at least one of a Wenzel or Cassie wetting state which may be altered by charging an electrode and wherein charging the electrode may generate an electroadhesive state.

In one embodiment, an electro-microstructured device may include at least one electroadhesive state which may cause adhesion to a target surface.

In one embodiment, an electro-microstructured device may include at least one electroadhesive state which may cause a change in a Wenzel-Cassie wetting state.

In one embodiment, an electro-microstructured device may include an electroadhesive state in combination with a Wenzel-Cassie state which may localize said device to a target surface.

In one embodiment, an electro-microstructure device may include charging of at least one electrode which may cause at least one part of the surface of the device to transition from one wetting state to another.

In one embodiment, an electro-microstructured device may include charging of at least one electrode which may alter a surface energy gradient on the device.

In one embodiment, an electro-microstructured device may include charging of at least one electrode in combination with the hierarchical microstructure which may generate a fluidic valving state.

In one embodiment, an electro-microstructured device may include charging of at least one electrode which may cause the electro-microstructured device to transition from at least one of a hydrophobic and hydrophilic surface to at least one of a hydrophilic and hydrophobic surface.

In one embodiment, an electro-microstructured device may include charging of at least one electrode which may create a wetting state comprising structured water.

In one embodiment, an electro-microstructured device may be configured to act as a braking system.

In one embodiment, an electro-microstructured device may be configured to act as a fluid/particle separation system.

In one embodiment, an electro-microstructured device may be configured such that said device can adhere to a wet non-conductive surface.

In one embodiment, an electro-microstructured device may be configured such that said device can adhere to a wet conductive surface.

In one embodiment, an electro-microstructured device may be configured such that said device may be switched between a hydrophilic state and a hydrophobic state which when said device is passed over a wet surface, water is removed from a portion of said wet surface.

In one embodiment, an electro-microstructured device may include a substrate having a hierarchical microstructure disposed thereon. The substrate may include a thickness wherein at least one electrode may be at least partially embedded within the thickness of the substrate. The electrode may further be connected to a charge source, wherein the at least one electrode is configured to provide a local charge when powered by the charge source, and wherein charging the electrode generates an electroadhesive state.

In one embodiment, an electro-microstructured device may be configured such that the local charge of the at least one electrode produces an electric field on a micrometer scale.

In one embodiment, an electro-microstructured device may include a first electrode and second electrode. The first and second electrodes may each be embedded within the thickness of the substrate. The first electrode may be configured to generate a positive charge, and the second electrode configured to generate a negative charge, and wherein the first and second electrodes may be adjacent to each other.

In one embodiment, an electro-microstructured device may include a substrate that is a dielectric.

In one embodiment, an electro-microstructured device may be configured such that a space between the adjacent first and second electrodes may include an electric insulator.

In one embodiment, the electro-microstructured device may include a plurality of electrodes which may be at least partially embedded within the thickness of the substrate and may be arranged in a spatially periodic pattern.

In one embodiment, the electro-microstructured device may include a hierarchical microstructure which may utilize a complex pillar. The complex pillar may include at least a first microfeature and a second microfeature, wherein the second microfeature may be disposed about the first microfeature. In some embodiments, the complex pillar may further include a third microfeature disposed about the second microfeature, a fourth disposed about the third, and a fifth disposed about the fourth, and so forth.

In one embodiment, the electro-microstructured may include a first microfeature having a height of 100 microns or less and a diameter of 20 microns or less.

In one embodiment, an electro-microstructured device may include a second microfeature has a height of 5 microns or less and a diameter of 2 microns or less.

In one embodiment, an electro-microstructured device may include a substrate which includes at least a portion that is hydrophobic. The electro-microstructured device may further include an electrode which may be arranged with the hierarchical microstructure to alter the substrate portion that is hydrophobic to a portion that is hydrophilic when the electrode is charged.

In one embodiment, the electro-microstructured device may include a substrate which includes at least a portion that is hydrophilic. The electro-microstructured device may further include an electrode that is arranged with the hierarchical microstructures to alter the substrate portion that is hydrophilic to a portion that is hydrophobic when the electrode is charged.

In one embodiment, the electro-microstructured device may include at least a portion of the electrode being disposed within the first microfeature.

In one embodiment, the electro-microstructured device may include at least a portion of the electrode being disposed within the second microfeature.

In one embodiment, an electro-microstructured device may include a surface having a thickness, and including a hierarchical microstructure disposed thereon. The hierarchical microstructure may include a layer of metallic particulates disposed thereon. Further, the device may include at least one electrode, the at least one electrode at least partially embedded within the thickness of the substrate and connected to a charge source, wherein the at least one electrode is configured to provide a local charge when powered by the charge source, and wherein charging the electrode generates an electroadhesive state.

In one embodiment, the electro-microstructured device may be configured such that the hierarchical microstructure may include a complex pillar. The complex pillar may include at least a first microfeature and a second microfeature, the second microfeature being disposed about the first microfeature.

In one embodiment, the electro-microstructured device may include metallic particulates having a diameter ranging between 0.1 to 1.0 microns.

In one embodiment, the electro-microstructured device may be configured such that the hierarchical microstructure includes two distinct microstructure regions, a first region wherein the metallic particulates comprise zinc, and a second region wherein the metallic particulates comprise silver.

In one embodiment, the electro-microstructured device may be configured such that the hierarchical microstructure includes two distinct microstructure regions, a first region wherein the metallic particulates comprise zinc, and a second region wherein the metallic particulates comprise gold.

DETAILED DESCRIPTION

Figure 1:
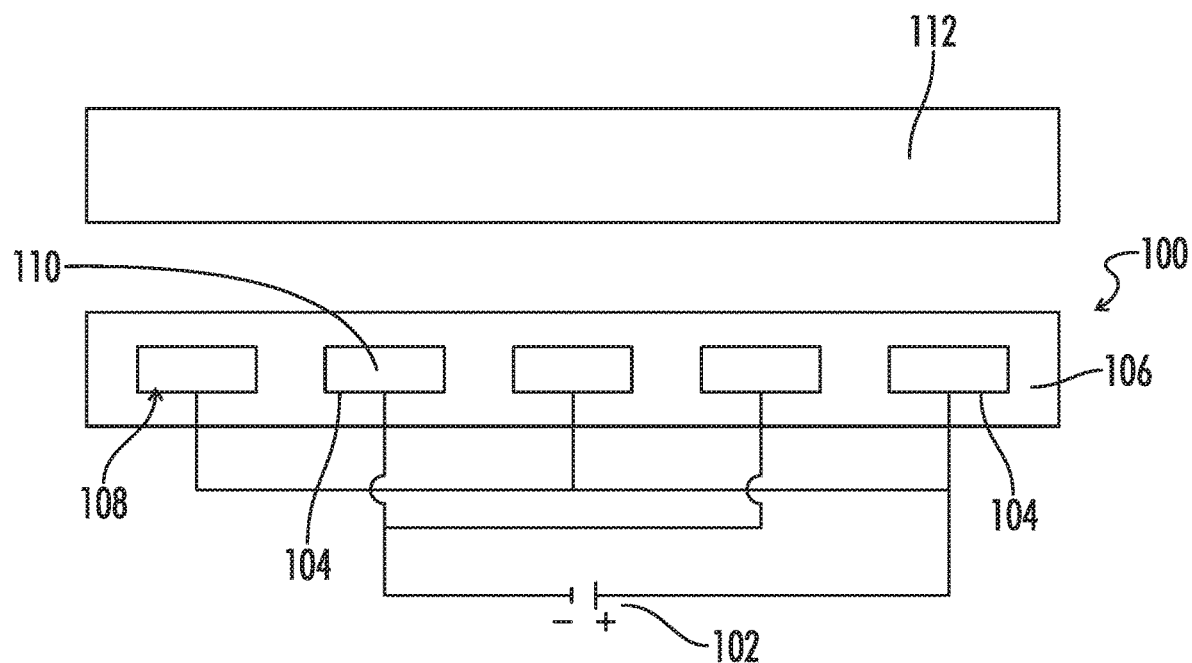
FIG. 1 is an embodiment of an electroadhesive device.

Exemplary applications of apparatuses and methods according to the present disclosure are described in this section. These examples are being provided solely to add context and aid in the understanding of this disclosure. It will thus be apparent to one skilled in the art that the present disclosure may be practiced without some or all of these specific details. In other instances, well known process steps have not been described in detail in order to avoid unnecessarily obscuring the present disclosure. Other applications are possible, such that the following examples should not be taken as limiting.

In the following detailed description, references are made to the accompanying drawings, which form a part of the description and in which are shown, by way of illustration, specific embodiments of the present disclosure. Although these embodiments are described in sufficient detail to enable one skilled in the art to practice the invention, it is understood that these examples are not limiting; such that other embodiments may be used, and changes may be made without departing from the spirit and scope of the disclosure.

As the term is used herein, "electroadhesion" refers to the coupling of two objects using electrostatic forces. Electroadhesion as described herein may use electrical control of these electrostatic forces to permit temporary and detachable attachment between two objects. This electrostatic adhesion holds two surfaces of these objects together by Coulomb attraction or by increasing the formation of Wenzel-Cassie domains between a device surface and a target surface. Wenzel-Cassie domain formation can be initiated or enhanced by increasing the surface energy of a microstructured surface.

As utilized herein, the term "hierarchical microstructure", when used to describe three-dimensional plastic webs, matrices of protrusions, porosities, and any surface geometrical modification which has been caused to conform to the surface of a three-dimensional forming structure so that both surfaces thereof exhibit the three-dimensional pattern of said forming structure, said pattern not readily visible to a normal human eye when the perpendicular distance between the viewer's eye and the plane of the microstructure is about 12 inches. It will be understood that the microstructures may be defined as any geometric shape and may include portions which are flat, rounded, spherical, pyramidal, pillar-shaped, or the like. The cross-section of a single microfeature of the microstructure may be circular, square, triangular, circular fluted, rectangular, or other geometric shape, including combinations thereof.

In general, as utilized herein the term "macroscopic" is used to refer to structural features or elements which are readily visible to a normal human eye when the perpendicular distance between the viewer's eye and the plane of the web is about 12 inches.

The present disclosure describes devices with a microstructured surface where part of the surface may comprise discrete areas of charge. In some embodiments, charge may be applied with a charge source and discrete electrodes embedded in a surface. In some embodiment, charge can also be generated environmentally. It will be understood that the application or development of a charge in one embodiment may be generated by multiple and/or different sources.

One embodiment utilizing electroadhesivity is illustrated in FIG. 1. An electroadhesive device 100 may include a charge source 102 which may be connected to electrodes 104 embedded in a dielectric substrate 106. The charge source 102 may charge one half of the electrodes 108 with positive charge and the other half of the electrodes 110 with negative charge. When the power source is switched on, the powered electroadhesive device 100 may attract substrate 112. Switching the charge source 102 off may cause substrate 112 and the dielectric substrate 106 to no longer be attracted to each other.

Figure 2:
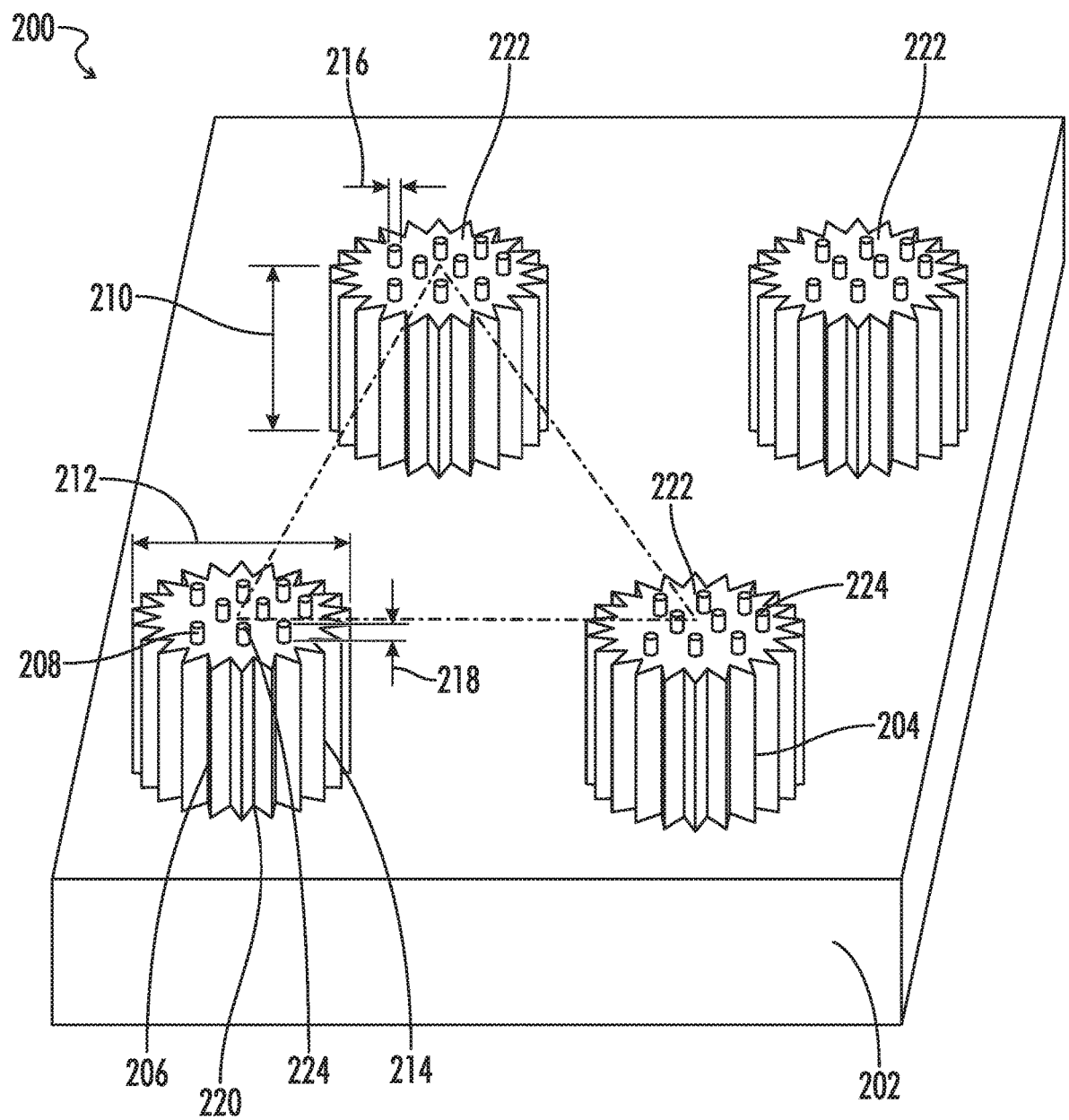
FIG. 2 is an embodiment of an electro-microstructured device.

Zinc is known to generate an electric potential when placed in a wet environment. Referring to FIG. 2, an electro-microstructured device 200 may include a flat polymeric substrate 202 which may include complex-pillars 204. The complex pillars 204 may be comprised of base pillars 206 and top pillars 208. The base pillars 206 may be spaced in a triangular array with a pitch (center-to-center distance) of 50 microns. Base pillars 206 may have a vertical height 210 of 100 microns and a diameter 212 of 20 microns. The vertical surface of the base pillars 206 may include triangular-profiled fins 214 having a width of 5 microns. Top pillars 208 may have a diameter 216 of 2 microns and a vertical height 218 of 5 microns. The top pillars 208 may be disposed on the top surface of the base pillars 206 being arranged in a triangular array with a pitch of 4 microns. In some embodiments, base pillars 206 may be of two types, depicted as type A 220 and type B 222. Type A 220 base pillars may include top pillars 208 disposed on the top surface, and further, the top surface 224 of the top pillars 208 may include zinc particulate deposits (0.1 to 1.0 microns in diameter). Type B 222 base pillars may include top pillars 208 disposed on the top surface, and further, the top surface 224 of the top pillars 208 may include silver particulate deposits (0.1 to 1.0 microns in diameter). The metal particulates may be adhered using a solution that may include the polymer substrate 202, for example a solution of ethanol and non-crosslinked polyurethane polymer.

When the device 200 is implanted in a body, the zinc may develop a voltage of −0.6 V and the silver may develop a voltage of +0.2 V. Type A and B pillars 220, 222 may be spaced gap between each pillar of approximately 30 microns, which is determined by the pitch measured center to center of each pillar minus the diameter of each pillar (50 micron pitch–20 micron diameter), which may generate a field gradient of 26 kV/m. The adhesive forces may be found to be proportional to the square of the field gradient.

The electroadhesive forces generated may be subject to the contact area between the electro-adhesive surface and the target surface, and also to the polarization property or dielectric constant of the target substrate. The contact area may be directly subject to the substrate surface textures of both surfaces, the electro-adhesive surface and target surface. As such, it may be necessary to take the substrate surface texture into consideration when developing the microstructure surface. One way to remove variability due to surface texture may be to construct the electroadhesive aspect on a multiplicity of scales, called hierarchical scaling.

The microstructured electroadhesive surfaces of the present disclosure may adhere to both conductive and insulating surfaces. The principles of generating electroadhesive forces on conductive versus insulating substrate materials are different and are further detailed herein.

Electroadhesion on conductive surfaces may be based on electrostatic induction as disclosed herein, whereas the electroadhesion on insulting surfaces may be due mainly to electrical polarization. The modelling of the electroadhesive forces on conductive substrates can be approximated by theories based on parallel capacitance, i.e., coplanar capacitance. The modelling of the electroadhesive forces on insulating substrates can be modelled by a complicated dynamic polarization process.

In the embodiment depicted in FIG. 2 the electrodes of type A 220 and type B 222 may be exposed. The fluid interface may act as the dielectric layer between the electrodes of type A and type B pillars 220, 222. In cases where the fluid interface is substantially conductive, electrodes may be coated with a polymer solution that includes a suitable dielectric. For conductive substrates, Coulomb forces may be dominant if the volume resistivity of the dielectric material covering the electrodes is greater than approximately $10^{14}$ Ωcm. In comparison, Johnsen-Rahbek forces may be dominant if the volume resistivity is between approximately $10^{10}$ and $10^{12}$ Ωcm.

Although a saturated electroadhesive force can be obtained for conductive substrates quickly (usually within 1 s), in some embodiments, a dynamic electrostatic attraction force generation process is desired. For example, in embodiments where short-term reversibility of the adhesion is desired, the reversibility may be obtained when the galvanic potential of the electrodes is slowed by tailoring the porosity of the dielectric and thus delaying the development of the galvanic potential. Embodiments as depicted in FIG. 2, where the electrodes are not galvanic, but are externally charged, may allow for many dynamic functionalities.

Electroadhesive devices of the present disclosure may use the electrostatic force between the target surface and the microstructured electroadhesive surface at the microscopic level. For Coulomb-type electrostatic surfaces, the electrostatic force may be generated by the dielectric polarization due to the electric potential difference. Based on the charge (or electrode) configuration, microstructured electroadhesive surfaces may be classified into two types: monopolar (plate-plate-capacitors) and bipolar (interdigitated electrodes). These basic electrode configurations may be disposed on a variety of hierarchical levels. When the electrodes are externally charged, then complex mixtures of these basic electrode configurations may further be possible.

Figure 3:
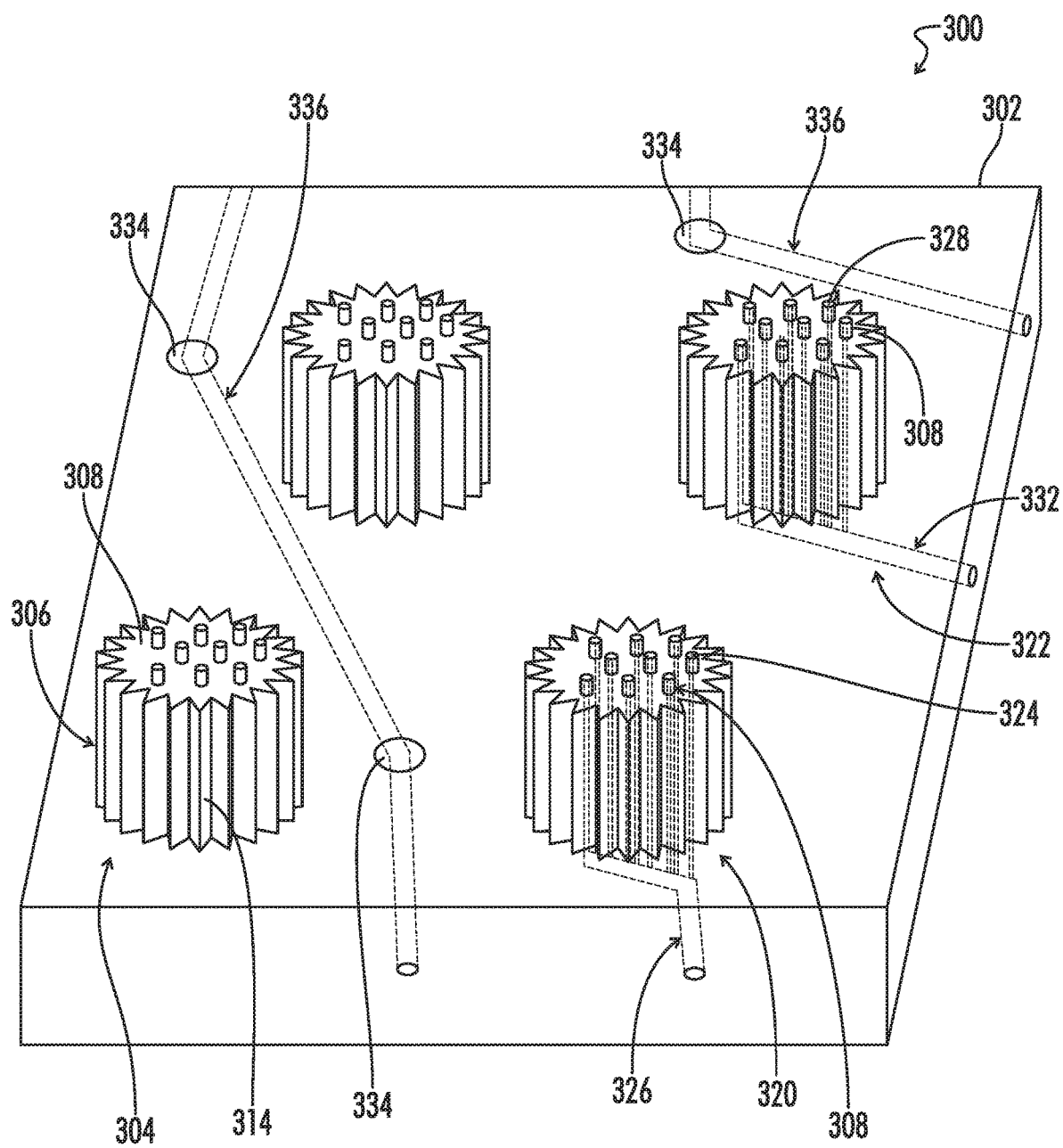
FIG. 3 is an embodiment of an electro-microstructured device.

Referring now to FIG. 3, an externally charged electro-microstructured device 300 comprising a flat polymeric substrate 302 may include complex-pillars 304. The complex-pillars may be comprised of base pillars 306 and top pillars 308. The base pillars 306 may be spaced in a triangular array with pitch (center-to-center distance) of 50 microns. Base pillars 306 may have a vertical height of 100 microns and may have a diameter of 20 microns. Additionally, the base pillars 306 may include triangular profile fins 314 having a diameter of 5 microns. Top pillars 308 may include a diameter of 2 microns a vertical height of 5 microns. The top pillars 308 may include a pitch of 4 microns center-to-center. In some embodiments, the top pillars 308 may be arranged in a triangular array.

In some embodiment, base pillars 306 may include two types of pillars 320, 322. Base pillars 306 may include type A pillars 320, which may comprise top pillars 308 disposed hierarchically thereon, and wherein the top surface 324 of the top pillars 308 may include a gold layer deposited thereon. Additionally, the top pillars 308 may further include conductors 326 which may be embedded in the substrate and traverse into the hierarchical complex. Base pillars 306 may further include type B pillars 322, which may comprise top pillars 308 disposed hierarchically thereon, and wherein the top surface 328 of the top pillars 308 may include a gold layer deposited thereon. Additionally, the top pillars 308 may further include conductors 332 which may be embedded in the substrate and traverse into the hierarchical complex. In one embodiment, the flat polymeric substrate 302 may include deposited gold circular layer 334 which may be in contact with conductors 336. In some embodiments, the gold layer may be coated or left exposed, or may include one area that is coated, and another area that is exposed.

In some embodiments, the electrode configuration may be obtained by charging the gold layer of type A pillars and gold layer of type B pillars with a potential difference. In one embodiment, +0.5 V on conductors 326 and −0.5 V on conductors 332 may create a charge by the potential difference of the conductors. In another embodiment, conductors 336 can be charged differently from conductors charging the gold layer(s). When gold layers 324 and 328 develop a field gradient, the electrode configuration may be approximately monopolar. When gold layers 324 and 328 are charged differently, the electrode configuration may be bipolar.

The electrode geometry and spacing as disclosed herein may act synergistically with the microstructured surface. In some embodiments, the microstructured surface is hierarchically stacked, which may provide the opportunity to layer electrodes in a monopolar configuration on different hierarchical levels. Within a hierarchical level, the electrodes may further be spaced in a bipolar configuration. For externally supplied charge, different regions of the electro-microstructured device may be monopolar and other regions bipolar.

Monopolar type microstructured electroadhesive surfaces may generate adhesive forces. In this embodiment, one of the electrodes may contact the target surface where a second electrode is insulated from the target surface by a dielectric layer. The target surface may be conductive such that a capacitor is formed between the electrode and the conductive target surface.

A bipolar type microstructured electroadhesive surface may typically be constituted by interlacing electrodes of two charged regions. In this embodiment, the electrodes may be insulated from the target surface by a dielectric layer. The space between the electrodes may be filled with an electrical insulator. For a microstructured device, a Wenzel-Cassie interface may be formed wherein air bubbles are trapped between electrodes. The air bubbles may act as insulators. In some embodiments, the trapped substance may be oil, attracted by a hydrophobic substrate. When the oil is trapped, e.g., between base pillars, it may act as an insulator and a dielectric.

When alternating positive and negative charges are induced on the adjacent electrodes and the device is placed in contact with a target surface, the electric fields may produce opposite charges on the target surface and thus may cause electrostatic adhesion between the electrodes and the induced charges on the target surface.

One important distinction of the monopolar configuration is that each hierarchical level may not be continuous. The configuration is advantageous because the non-continuity creates "holes" or gaps between the plates. This configuration may be counter-intuitive based on the prior art because the electric field may be highest in the dielectric between the two electrodes, not on the target surface to which the device contacts.

The gaps may allow the electric field to essentially "leak" through to the target surface. This "leakage" may create a stronger electric field than the conventional bipolar design. This is because the hierarchical design may allow the gap between electrodes to be significantly decreased. Gap size may have a strong effect on adhesion force per unit area. In this configuration, smaller gaps may be possible because the hierarchical design may allow for a dielectric with a high voltage breakdown constant compared to a standard bipolar design.

Further considerations as to the gap size between electrodes is dependent on any residual material, external particles, and trapped air in the gaps. Because of the susceptibility of the gaps to these issues, the addition to the surface of microstructures may play an important role. By designing the microstructure to have a particular juxtaposition of surface energies, interface constituents can be attracted or repelled.

Generally, the prior art has relied on electrode structure as being macroscopic, typically greater than several millimeters. In such macroscopic designs, the electroadhesive stresses and energy can be estimated by empirical equations. However, these equations fail at the microstructured level. Furthermore, there is a lack of theoretical models to reveal the relationship between the adhesive force and the microstructure parameters, which are disclosed herein.

Optimal design principles are unavailable for electroadhesive and electrorepulsive devices as used in the prior art. Some progress has been made on the electrostatic-levitation problem, but this model applies to macroscopic electrodes. When microscopic electrodes are involved, one must pay particular attention to optimization of the electric charging rate with respect to the geometrical parameters of electrodes, if one's goal is to create a surface that is cyclically electroadhesive and non-electroadhesive. One example may include the development of a foot surface of a wall-climbing robot.

It will be understood that the following examples may employ four-layer and five-layer hierarchical textures, although in practice any number of layers (so long as hierarchical) may be sufficient for most applications.

With regards to electroadhesion on a conductive target surface, an electrostatic induction phenomenon may occur where the formation of negative charges on one side and positive charges on the opposite side of a target conductor may be induced by an external electrostatic field produced by a charged electrode embedded in an insulator comprising the microstructured surface.

It will be understood that "conducting materials" may generally refer to materials consisting of a large amount of mobile free charge carriers. In some embodiment, wet tissue may cause the concentration of free mobile charge carriers to be of the same order as that of the number of molecules. These charges may rearrange themselves quickly and easily. Equal and opposite charges may be induced on the surface of a target conductive substrate after the application of a high field gradient on the electro-microstructured surface/device. The electroadhesive forces between the device and the target surface may then be formed.

In some embodiment, the electro-microstructured device may be monopolar, bipolar, and/or even tripolar. In the prior art, the dipole design has generally been the most frequently used design in electroadhesive applications. For coulomb type dipolar electro-microstructured devices, the electroadhesive forces between the device and the target substrate may be derived from a series of parallel connections of several ideal capacitors having dielectrics in series. Specific attention may be paid to particular parameters to effectively product the electroadhesive forces including the air gap between the device and the target substrate, the dielectric thickness, the capacitances of the dielectric material, the capacitance of the interface between the dielectric and the target substrate surface. The total capacitance between the device and target substrate, and between the pad and substrate, may depend on the number of electrodes, the effective electroadhesive area, the permittivity of the interface volume and the relative permittivity of the dielectrics. The electroadhesive force varies as the square of the total capacitance.

The Johnsen-Rahbek force occurs when imperfect dielectrics with finite volume resistivity, such as semi-conductive materials interact with high charge mobility target substrates. Current leakage or charge transfer may occur through the contacting points between the device and the target substrate. In some embodiments, a strong electrostatic attractive force may be generated at the interface by the accumulation of charge in the non-contact areas. The small gaps characteristic of hierarchical microstructures surfaces may be responsible for these strong Johnsen-Rahbek adhesion forces.

The adhesion of a Johnsen-Rahbek electro-microstructure device may depend on the potential difference applied across the interface, rather than a field gradient applied through the dielectric layer. Johnsen-Rahbek electrostatic attractive force is independent of the dielectric material between the device and target substrate. Particular parameters that may be identified to producing these forces in microstructured devices may include the capacitance of the non-contact areas, the potential difference across the interfaces, and the potential difference across the non-contacting areas. In some embodiments, the stacked hierarchical structure may be optimal for both gap placement and electrode placement.

Generally, adhesion due to the Coulomb potential may be much smaller than the Johnsen-Rahbek force, especially in embodiments where the interface gap is smaller than the thickness of the dielectric material.

In embodiments for cyclic adhesive devices, the detachment time may be much faster when the Coulomb force is utilized. Additionally, less current leakage in the Coulomb configuration may result in lower power consumption.

In some embodiments, the electro-microstructured device may involve the total polarization comprising the sum of the electronic polarization, the ionic polarization, the orientational polarization, the space charge polarization, the hopping polarization, the interfacial polarization, the spontaneous polarization, and other types of polarizations such as the nomadic polarization.

For embodiments with contacting electro-microstructured devices, the orientational polarization and interfacial polarization may account for generation of the electroadhesive forces. The electroadhesion phenomenon can be contactless both on conductive substrates and insulating substrates. For embodiments with non-contacting electro-microstructured devices, the atomic and electric polarization may account for the generation of the electroadhesive force.

It should be understood that in devices of the current disclosure, electroadhesion may strengthen over time. The steady state value of the adhesion force may generally be much larger than the initial value. The time period to reach the steady state value may depend on various design parameters.

Embodiments which include particular monopolar electrode geometry, the electrodes may generally be arranged in a spatially periodic pattern. Generally, the length of the electrode may be much larger than its width and/or thickness, and the electrode area may be much larger than the area between individual electrodes. For this reason, symmetric patterns may be preferred in some embodiments.

One of skill in the art will appreciate the inclusion of hierarchical structures in the various embodiments of this disclosure. Analyzing the performance of a hierarchically structured electroadhesive device, one may consider each hierarchical scale as an added layer and performs calculations as if the device were a composite device with an effective dielectric constant. The effective dielectric constant may be evaluated by the parallel mixing rule. The calculation reveals that electroadhesion may be reduced as the height of each hierarchical layer increases. Therefore, in some embodiments, the height of the hierarchical layers may decrease as the dimensions decrease, thus more layers may increase the electroadhesion properties of the device.

Some embodiments may combine the electroadhesive force with the van der Waals force of the microstructured surface to generate a strong adhesion. The microstructures having dimensions down to the micro or even nanoscale may generate strong adhesive forces. Therefore, the very smallest structures may not only decrease the gap between the device and target surface, but also enhance the attraction force in absolute terms. In one embodiment an electroadhesive device may be capable of generating both electroadhesive and van der Waals forces.

Another parameter that may be of use is the inclusion of semi-conductive materials for an insulation layer or a microstructure substrate which may enhance the electrostatic clamping forces at lower electrical field levels. This increased clamping force may be attributable to the Johnsen-Rahbek effect that may take place at the boundary between the metal electrode and the surrounding semi-conductive material. Accordingly, lower voltages and currents can be used to achieve the same clamping forces when using a semi-conductive insulator rather than a fully dielectric insulator.

Although it is known that polyurethanes work well as semi-conductive materials, various other materials may also be used. These other semi-conductive materials may typically have a bulk resistivity that ranges from about 107 to 1013 Ωm, with a more preferable range being about 109 to 1012 Ωm. Various polyurethanes, nitrile halogenated or latex rubbers, and certain silicones, for example, may be used as a suitable insulating material for some embodiments of the disclosed electroadhesive devices. One example of a material that works well is the Deerfield polyurethane PT7811.

In some embodiments, additive particles, dopants, and/or solutions may be included to enhance the conductivity of an otherwise insulating polymer. These additive particles may include, but are not limited to, carbon, quaternary salts, and plasticizers such as Dioctyl Phthalate or DiIsoOctyl Phthalate.

In one embodiment using such material, it may be able to achieve clamping forces up to about 70 psi. In one embodiment that utilizes a coating over the electrodes rather than a full insulating layer, the coating may be of about 10 to 30 micrometers thick. In other embodiments, the use of semi-conductive insulators may allow for the use of insulating layers that may be up to 100 microns thick. In various embodiments, the insulation material may include a compliant material with an elastic modulus less than about 1 GPa, which may facilitate better clamping.

In addition to the use of highly resistive materials in some embodiments of the disclosed adhesive devices, semiconducting materials with different properties may also provide benefits when applied as the electrodes themselves. In one embodiment, various polyurethanes or other materials may be used at least on the surfaces of one or more electrodes. For embodiments with highly resistive electrodes, a static-dissipating conductive strip material may have a surface resistivity ranging from about 0.1 to 1000 MΩ/square, a thickness of about 1 to 50 micrometers, be relatively inexpensive and readily available, and be mechanically and electrically robust. More preferably, the surface resistivity may range from 1 to 100 MΩ/square. It is contemplated that one embodiment may include carbon particles mixed with relatively soft polyurethanes. Such polyurethanes can be sprayed on, dip coated, or otherwise applied to the appropriate electrode surface in any suitable manner. Other alternatives for electrode materials may utilize nanotubes, which may be conductive at much lower loading levels. Still another option may include graphite electrodes with a thin coating as a sealing layer that may be applied, such as by spraying. Embodiments with this sealing layer may include very low carbon black loading, or in some embodiments none at all. Other options may involve adding a plasticizer or a soft polyurethane blended in tetrahydrofuran. Diisooctyl phthalate may also be used as a polyurethane plasticizer. Various specific examples of materials that have been found to work well include Dupont 100XC10E7, Scicron ABF-300, and TMF-300 materials.

The following are embodiments which may be directed to the design of electro-microstructured surfaces. These embodiments are not meant to be exhaustive, but rather examples of the principles disclosed to guide one in the practice of this patent.

Example 1. Tissue Scaffold with Electro-Selection of Cell Type

Biomaterials are widely used in the medical field to maintain, improve, and/or restore diseased tissues or organs.

The successful integration of biomaterials with host tissue may depend on substratum surface properties, as well as host tissue quality and the surrounding environment. The embodiment defined more fully below may utilize these various factors to allow better incorporation of the host tissue and biomaterial.

Figure 4:
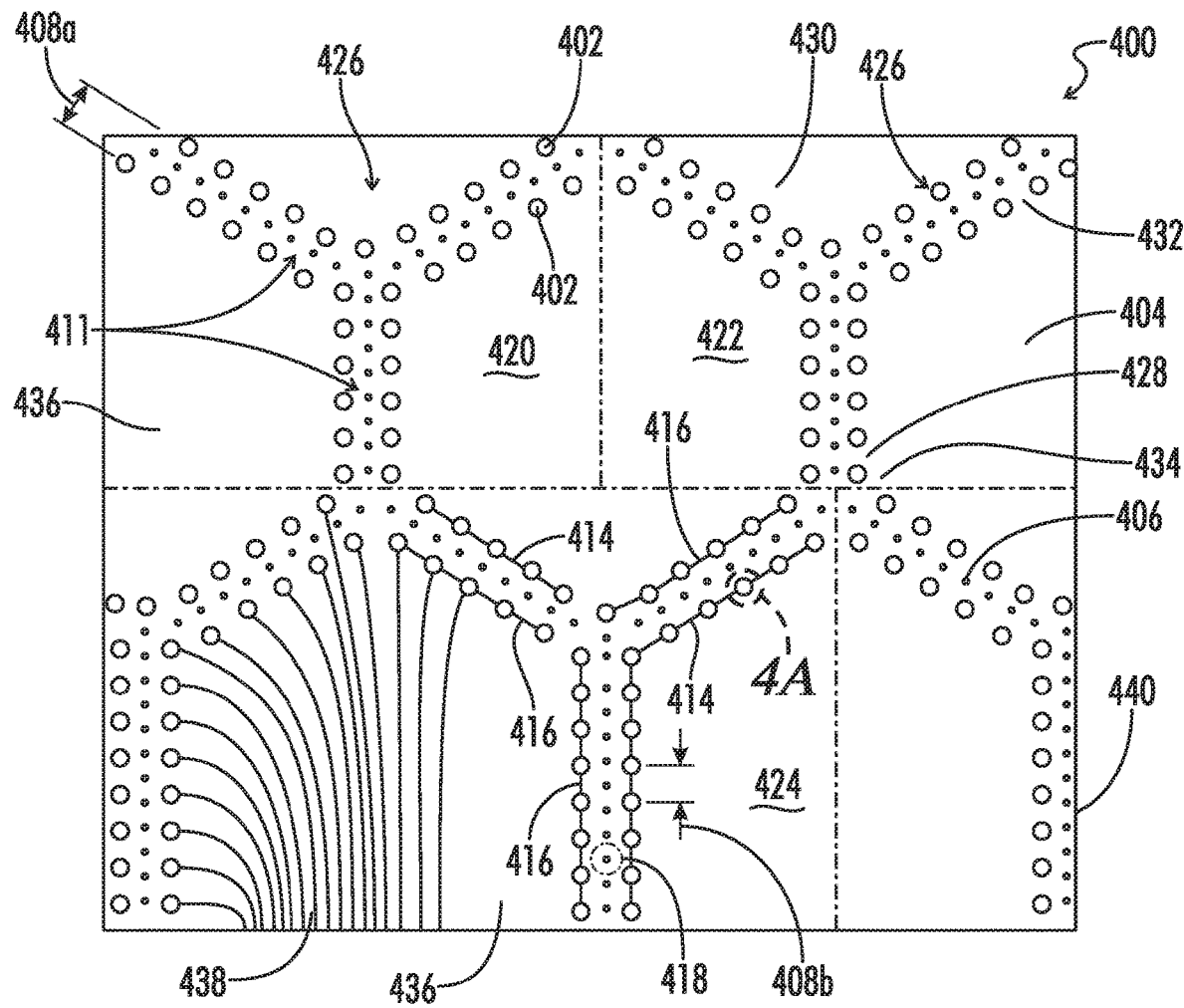
FIG. 4 is an embodiment of a tissue scaffold with electro-selection of cell type.
Figure 4A:
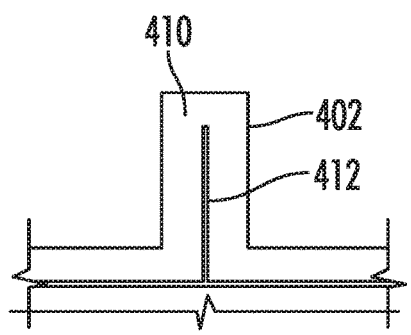
FIG. 4A is a side view of one of the structures as designated in FIG. 4.

Referring to FIG. 4, a tissue scaffold 400 may include microstructured pillars 402 arranged on a polymer substrate 404. The microstructured pillars 402 may be arranged in rows. In some embodiment, the rows of microstructured pillars 402 may further include smaller pillars 406 disposed between two opposing rows of microstructured pillars. Two opposing rows of microstructured pillars 402 may include a spacing of approximately 10 microns 408a between the two rows. Additionally, the microstructured pillars 402 within the same row may also be spaced approximately 10 microns apart, 408b. Microstructured pillars 402 may include an interior portion 410 which may include electrodes 412 along the centerline of the microstructured pillars as shown in FIG. 4A. Some electrodes 412 may be electrically connected by conductors 414, 416. The conductors 414 may have a positive potential, and the conductors 416 may have a negative potential, thereby a field gradient may be created in region 418 located between the two opposing rows of microstructured pillars 402. The opposing rows of microstructured pillars 402 may be positioned such that a symmetry relation is created, as illustrated by squares 420, 422, and 424. Within each square is a Y-shaped configuration 426 with base 428 and left bifurcation 430 and right bifurcation 432. Left and right bifurcations may connect to an adjacent base as illustrated at 434, thus creating a repetitive pattern on the polymer substrate 404.

In some embodiments, microstructured pillars 404 may be approximately 10 microns tall and approximately 3 microns in diameter with a circular cross section. Smaller pillars 406 may be approximately 3 microns tall and approximately 1 micron in diameter with a circular cross section. In one embodiment, open region 436 of the substrate surface 404 may be populated with ridges 438, and wherein the ridges may be approximately 10 microns tall and approximately 3 microns in thickness with a rectangular cross section.

In some embodiments, cells disposed about the periphery 440 of the tissue scaffold 400 may be caused to move along the pathways 411 between opposing rows of microstructured pillars 402. In some embodiments, the Y-shaped configuration 426 may encourage the formation of blood vessels by endothelial cells.

Figure 5:
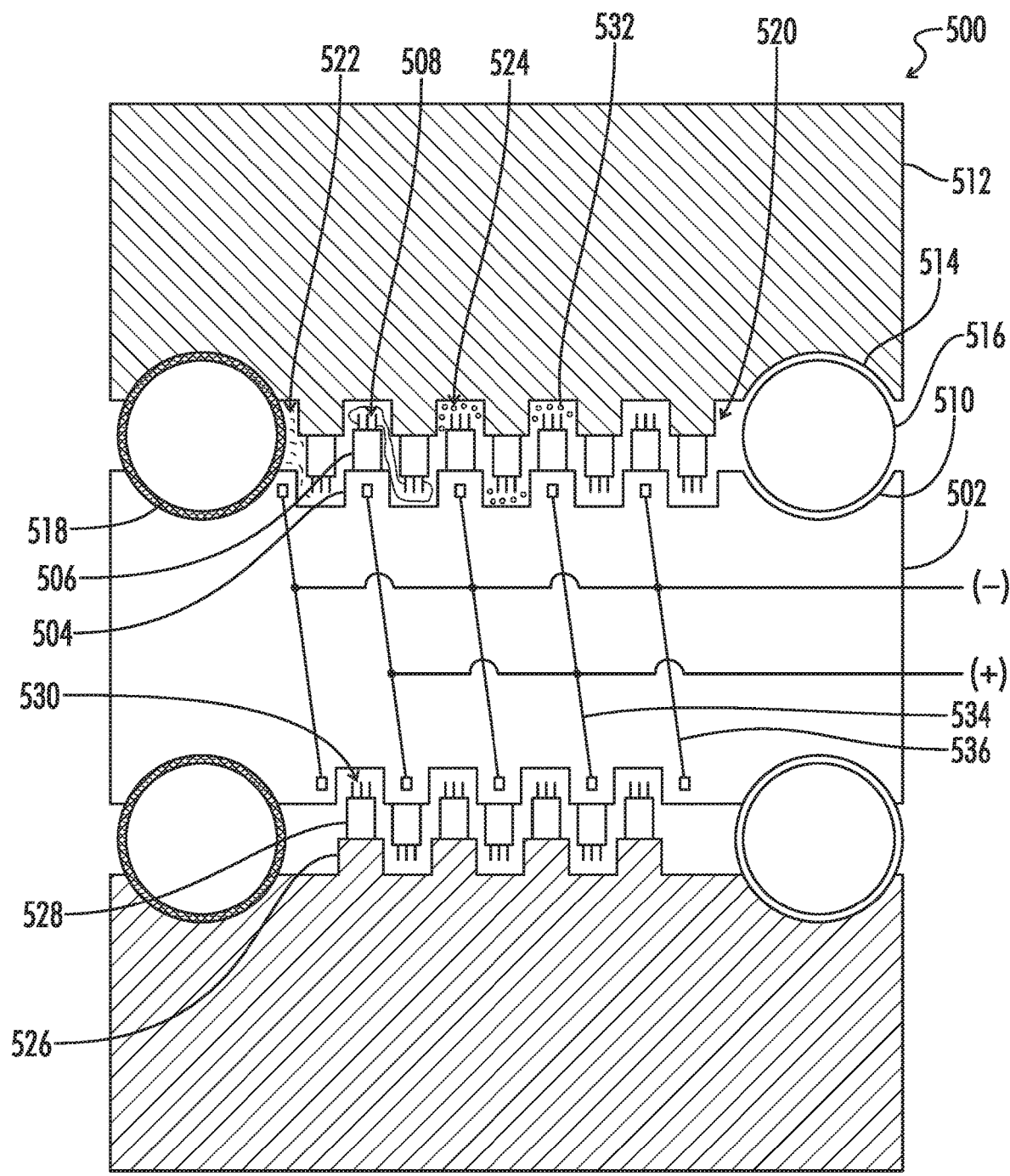
FIG. 5 is an embodiment of a contactless brake utilizing reversible Wenzel-Cassie domains.

Example 2. A Contactless Brake Utilizing Reversible Wenzel-Cassie Domain Creation Referring to FIG. 5, a braking system 500 may include a braking element 502 and a rotating element 512. Braking element 502 may include with a surface that comprises a first hierarchical level 504, a second hierarchical level 506, and a third hierarchical level 508. In some embodiments, the first hierarchical level 504 may have a square cross-section. In some embodiments, the second hierarchical level 506 may have a circular cross-section. And in some embodiments, the third hierarchical level 508 may have a circular cross-section. In some embodiments, the braking element 502 may include two or more bearing channels 510.

In some embodiments, rotating element 512 may include a surface that may be smooth. In other embodiments, rotating element 512 may include a surface with microstructures disposed thereon. In some embodiments, the rotating element 512 may include a surface with both a smooth portion and a microstructured portion. In some embodiments, the rotating element may include at least two bearing channels 514. The bearing channel 510 of the braking element 502 and the bearing channel 514 of the rotating element may be aligned and create a cavity. The cavity in some embodiments may contain at least one ball bearing 516. Additionally, the cavity may also contain an anti-friction composition 518 that coats and/or surrounds the at least one ball bearing 516. In some embodiments, the bearing channels 510 and 514 may be located along the peripheral sides of the braking element 502 and rotating element 512, thereby creating an interior chamber 520. In some embodiments, the interior chamber 520 may be sealed and in which is contained a hydrophilic liquid 522 and an insoluble hydrophobic liquid 524. The volume of the hydrophilic liquid 522 and insoluble hydrophobic liquid 524 may vary dependent on the application. In some embodiments, there may be more hydrophilic liquid 522 volume than insoluble hydrophobic liquid 524, In other embodiments, there may be more insoluble hydrophobic liquid 524 volume than hydrophilic liquid 522. And in some embodiments, the volumes of each liquid 522, 524 may be approximately the same. It will be understood that while the term "liquid" is used herein, the term will also encompass semi-liquids, gels, viscous compositions, and the like. In some embodiments, the insoluble hydrophobic liquid 524 is of a smaller volume than the hydrophilic liquid 522 such that when braking element 500 is in motion the hydrophobic liquid may form small balls 532 while being disposed in the hydrophilic liquid.

Some embodiments of the rotating element 512 may include the surface comprising a first hierarchical level 526, a second hierarchical level 528, and third hierarchical level 530. The first hierarchical level 526, may have a square cross section. The second hierarchical level 528 may have a circular cross section. The third hierarchical level may also have a circular cross section. In some embodiments, the combined hierarchical microstructures 526, 528 and 530 may produce a hydrophobic effect. Similarly, in some embodiments, combined hierarchical microstructures 504, 506, 508 of the braking element 502 may also produce a hydrophobic effect.

As a practical perspective, one embodiment of the braking system 500 may be used such that the braking element 502 is unpowered and the rotating element 512 is rotating and in motion. When this state occurs, the small balls 532 of hydrophobic liquid 524 may be caused to come into contact with microstructures 528, 530, of the rotating element 512 and microstructures 506, 508 of the braking element 502. In this embodiment, the small balls 532 may themselves act as microscopic ball bearings. The hydrophilic liquid 522 may flow, or move, in the voids created between microstructures 526 and the braking element surface, and between microstructures 504 and the rotating element surface.

In some embodiments, the first hierarchical level 504 may contain alternating electrodes 534, 536 between adjacent microstructures. Electrode 534 may be positively charged and electrode 536 may be negatively charged. Powering electrodes 534 and 536 may cause the second and third hierarchical microstructures 506, 508 to transition from a Cassie state to a Wenzel state. When this transition occurs, the hydrophobic liquid 524 may migrate from second and third hierarchical microstructures 506, 508 disposed on the braking element 502 to the second and third hierarchical microstructures 528, 530 on the rotating element 512. This transition of the hydrophobic liquid may create locking Wenzel-Cassie state which causes to the rotating element 512 to decrease its rotation.

Figure 6:
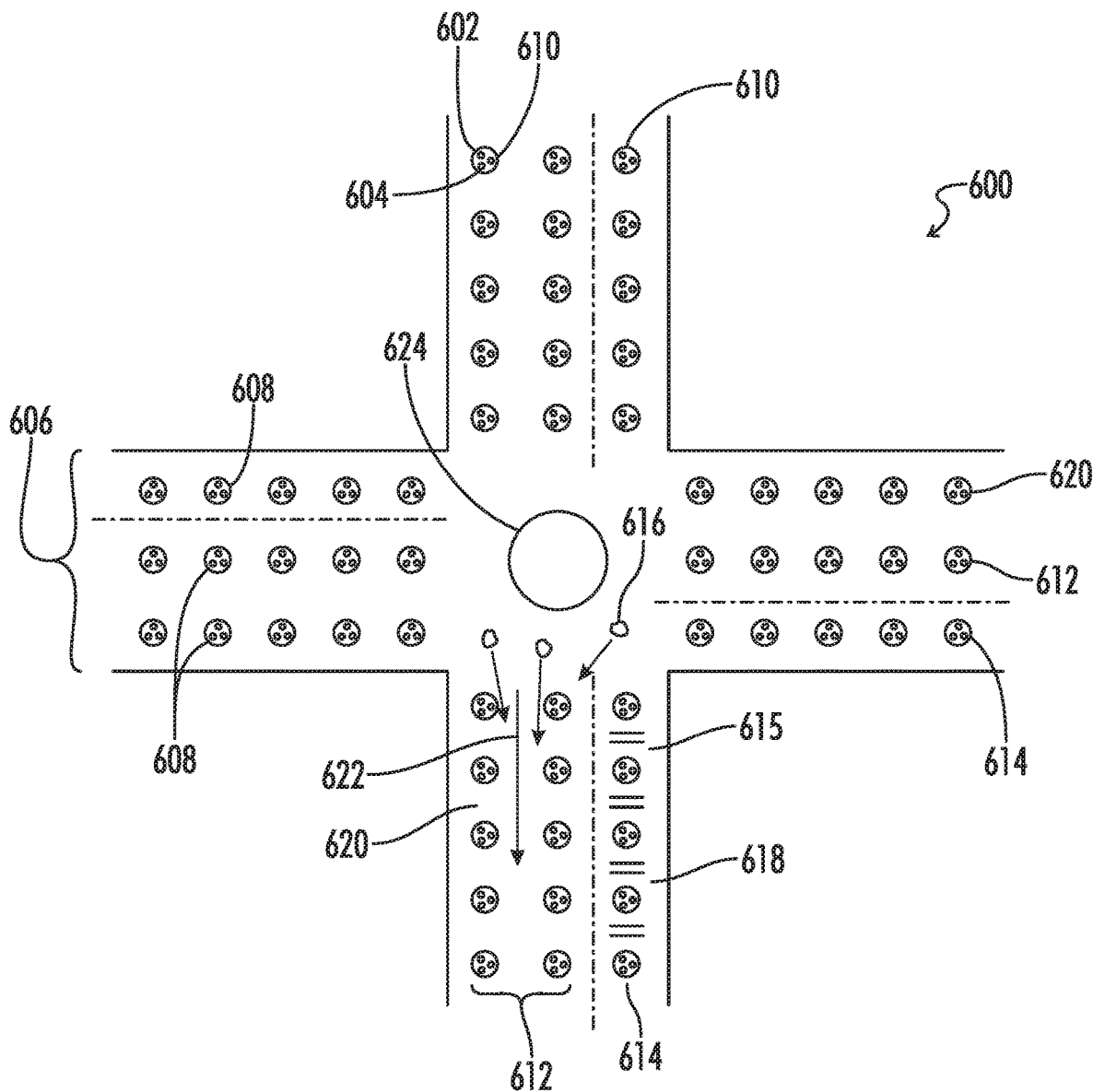
FIG. 6 is an embodiment of a blood filtering device using structured water valving and charge repulsion.

Example 3. A Blood Filtering Device Using Structured Water Valving and Charge Repulsion Sialylated glycoproteins on the surface of red blood cells may be responsible for generating a negative electric zeta potential. Referring to FIG. 6, a blood filtering device 600 may include a surface having complex pillars disposed thereon. The complex pillars may be hierarchically arranged and include a first pillar 602 and a second pillar 604. The second pillar 604 may be arranged on top of the first pillar 602 in a hierarchical fashion. In some embodiments, the complex pillars may be arranged in rows 606. In some embodiments, the rows of complex pillars may further be arranged such that multiple rows 608 are located adjacent and parallel to each other creating columns.

In some embodiments, each of the first pillars 602 may include an electrode 610 associated with it. In embodiments with at least three parallel rows 608, the rows may be electrically configured such that two adjacent columns 612 may be of the same electrical charge, and the third column 614 may be of the opposite charge. For example, the two adjacent columns 612 may be positively charged and the third column 614 may be negatively charged. Due to such a configuration, the space between the adjacent columns 612 and 614, having opposing electrical charges, creates a structured water state 615 in which the polarity of the water causes the water molecules to align and may exclude particulates such as red blood cells 616. Embodiments having this or a similar configuration may result in a valve-like mechanism that may exclude particulates but allow water flow in the channel 618. The two positively charged columns of pillars 612, 620 may undergo a sinusoidal variation in potential which may cause red blood cells 616 to be attracted and then pass in direction 622 along a line of spatially varying surface energy.

In some embodiments, an inlet 624 may be configured to allow ingress of whole blood under slight pressure. The ingress of whole blood through inlet 624 may then travel along the rows and columns of microstructured pillars. While, FIG. 6 shows a plane of orientation perpendicular to gravity, it is anticipated that other embodiments may include different configuration which may be advantageous. In on embodiment, arranging the parallel rows and columns vertically may create a chimney effect. Furthermore, it may be effective to arrange the red blood cell conducting channels in the direction opposite of gravitational pull and the filtrate conducting channels in the direction of the gravitational force. In this opposing-type configuration, one imagines a chimney-drain configuration, where the chimney effect may be achieved by a spatially varying gradient and the drain effect may be achieved by gravitational force. In the filtration of other constituents of blood, such as platelets, this chimney-drain arrangement may be reversed.

Example 4. A Hierarchically Electro-Microstructured Adherent Device

Figure 7:
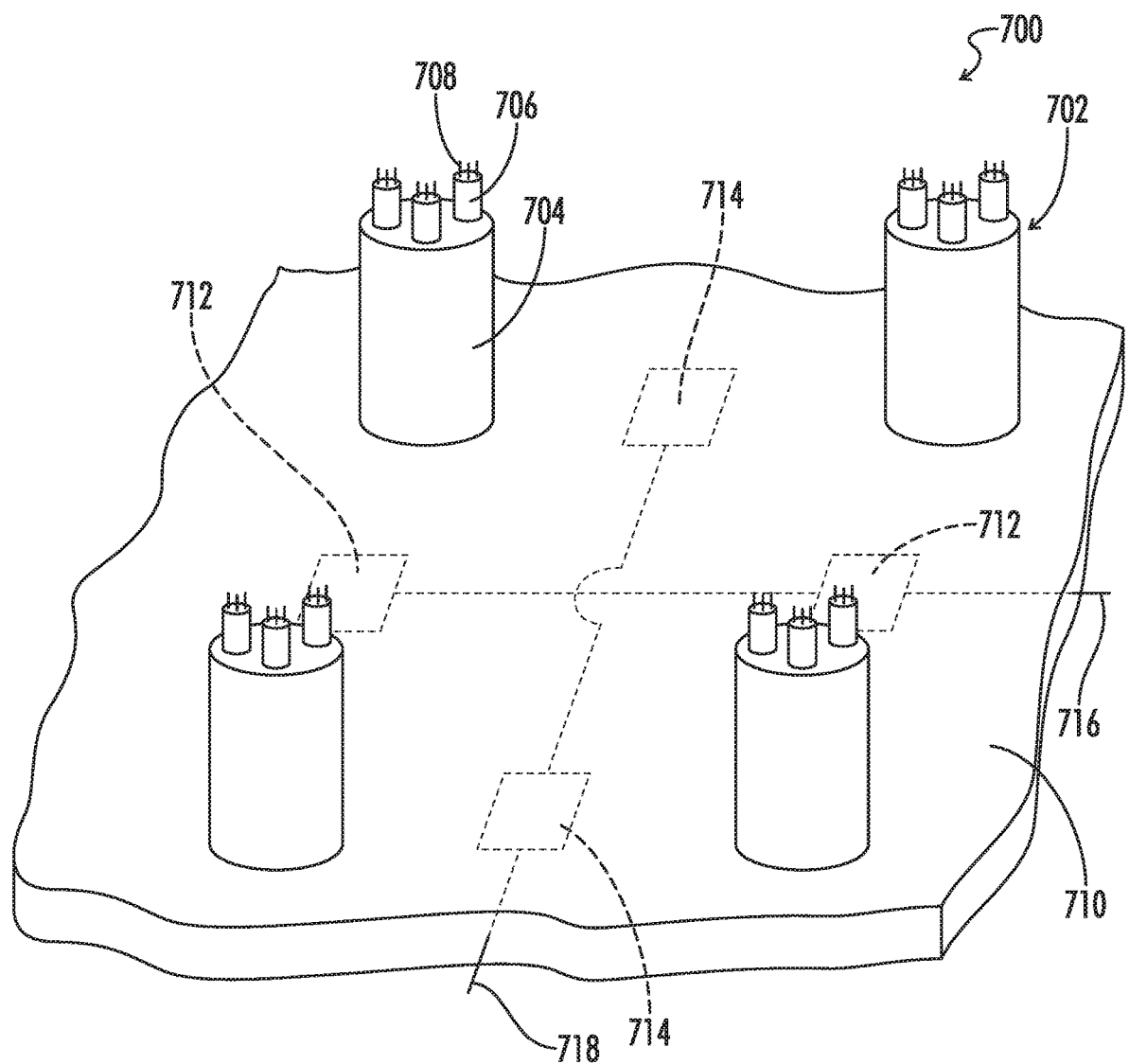
FIG. 7 is an embodiment of a hierarchically electro-microstructured adherent device.

Referring now to FIG. 7, electro-microstructured adherent device 700 is disclosed and may include complex pillars 702. In some embodiments, the complex pillars 702 may be flexibly pliant, and in some embodiments, the complex pillars may be rigid. In some embodiments, the complex pillars 702 may be arranged in a regular pattern or in a random pattern. In certain embodiments, the random pattern of complex pillars 702 may be preferred to promote adhering of the device 700 to surfaces of varying microstructure. The complex pillars 702 may be of any cross-sectional shape. In some embodiments, the cross-section may be circular or elliptical. In embodiments with an elliptical cross section, the major axes of the ellipses may be arranged randomly or in a concentric pattern.

In some embodiments, complex pillars 702 may be comprised of first pillars 704, on which are stacked second pillars 706, and on which are further stacked third pillars 708, thus incorporating a hierarchical structure. The first pillars 704 may be spaced apart from each other on centers of length equal to their total height of the entire hierarchical structure. In some embodiments, the first pillars 704 may be between 100 to 1000 microns in height. The second pillars 706 may be between 35 and 100 microns in height. The third pillars 708 may be between 1 and 35 microns in height. In some embodiments, the third pillars 708 may be spaced on centers of length between 0.1 and 1.5 the length of the pillars 708 height.

In some embodiments, the complex pillars 702 may be disposed on a substrate 710 of the device 700. The substrate 710 may have a thickness, into which are embedded positively charged electrodes 712 and negatively charge electrodes 714. In some embodiments, adjacent to every positively charged electrode 712 is a negatively charged electrode 714.

In some embodiments, electroadhesion of the device 700 to a target surface may be generated by charging electrodes 712,714 via conductive lines 716, 718.

Figure 8:
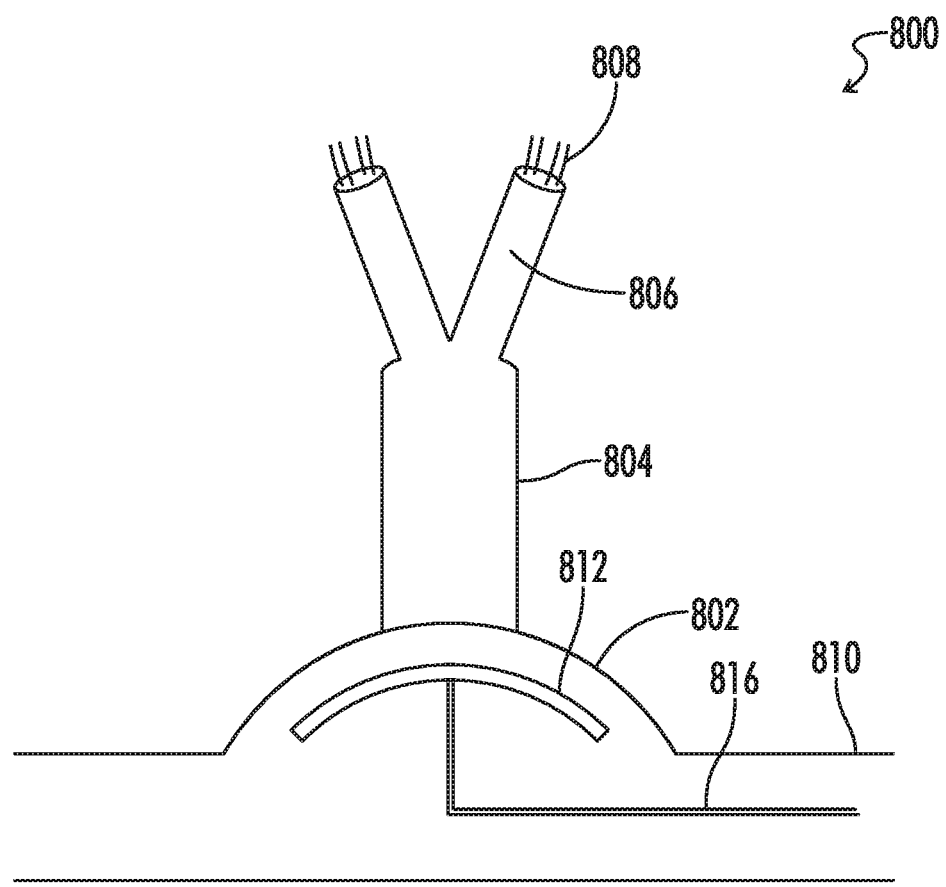
FIG. 8 is an embodiment of a 4-level hierarchical arrangement of electrodes and surface microstructures on an electro-microstructure device.

Example 5. A 4-Level Hierarchical Arrangement of Electrodes and Surface Microstructures on an Electro-Microstructure Device Referring now to FIG. 8, a single 4-level microstructure 800 is illustrated. In some embodiments, the microstructure 800 may be used to replace the complex pillars 702 as disclosed in Example 4. In some embodiments, the overall electrode structure of Example 4 may remain the same with the 4-level microstructure 800. In one embodiment, the first microstructure 802 may be hemispherical and is disposed about the surface 810 of the device. The second microstructure 804 may be cylindrical and disposed about the first microstructure 802. The third microstructure 806 may be cylindrical and disposed about the second microstructure 804. The fourth microstructure 808 may be of a circular, fiber-like construction and disposed about the third microstructure 806.

Electrode 812 may be hemispherical and contoured in a similar geometry as to the first microstructure 702. Electrode 812 may be associated with and charged by lead 816.

Figure 9A:
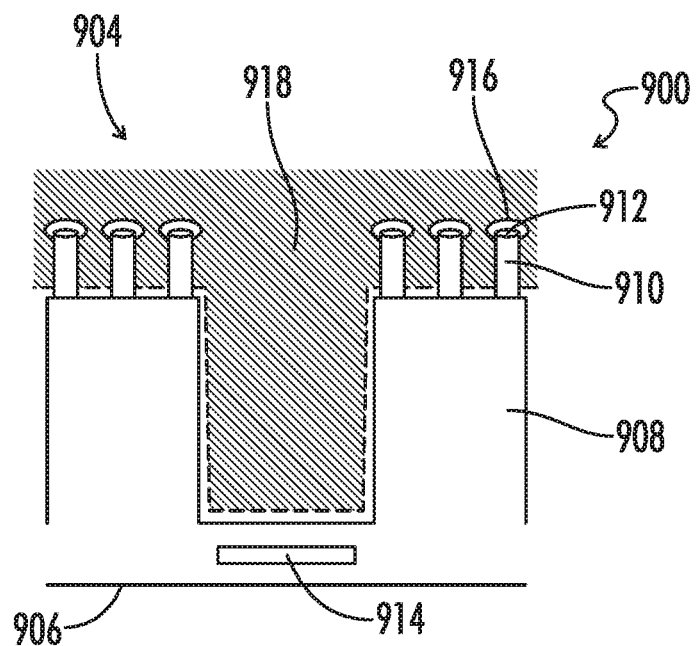
FIGS. 9A and 9B are embodiments of a superhydrophilic (9A) and superhydrophobic (9B) transforming electro-microstructured device.
Figure 9B:
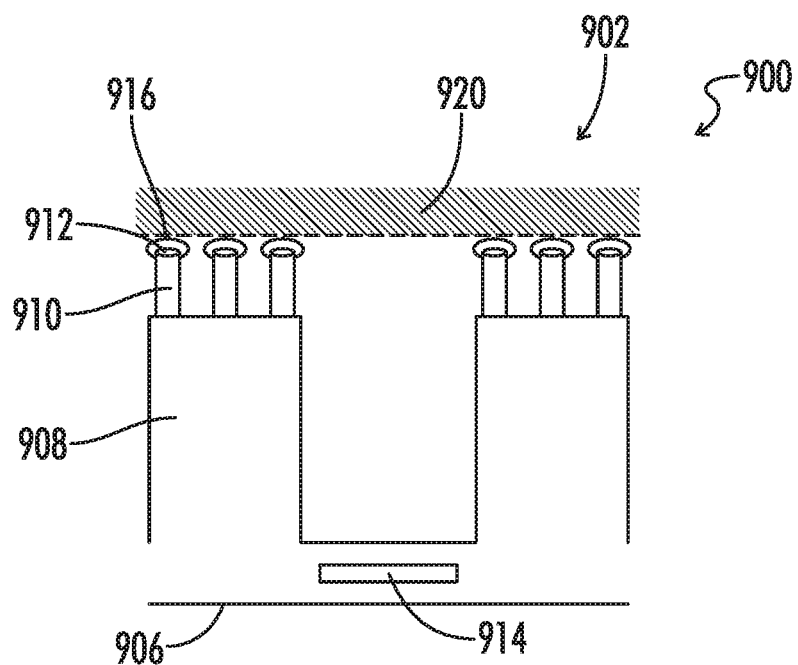

Example 6. A Superhydrophobic/Superhydrophilic Transforming Electro-Microstructured Device Referring now to FIGS. 9A and 9B, a superhydrophobic/superhydrophilic transforming electrostructure device 900 is illustrated. FIG. 9A depicts a superhydrophilic state 904, and FIG. 9B depicts a superhydrophobic state 902. The electrostructure device 900 may include a substrate layer 906. Disposed about the substrate layer 906 may be first pillars 908 and second pillars 910. The first and second pillars 908, 910 may be arranged hierarchically. In some embodiments, the first pillars 908 may have a cross-section that is hexagonally shaped. In some embodiments, the second pillars 910 may have a cross-section that is circular. In some embodiments, the substrate layer 906 may include a thickness in which is disposed electrodes 914. In some embodiments, a second electrode 912 may be disposed about the second pillars 910. Further, in some embodiments, a final hydrophobic coating layer 916 may also be included.

In one embodiment, the second electrode 912 may be disposed about the top of the second pillar 910. The second electrode 912 may be arranged to cover the entirety of the top surface of the second pillar 910 or may partially cover the top surface. In one embodiment, the electrode may be of an opposite charge as the first electrode 914. The first electrode 914 may be disposed within the thickness of the substrate layer 906 and may generally be located in the areas between the first pillars 908. When electrodes 912, 914 are of opposite charge then the structure may have superhydrophilic characteristics (FIG. 9A) and achieve a Wenzel wetting state 918. When electrodes 912, 914 are of the same charge then the structure may exhibit superhydrophobic characteristics (FIG. 9B) and achieve a Cassie non-wetting state 920.

Example 7. A Spiral Field Effect Electro-Microstructured Device

Figure 10:
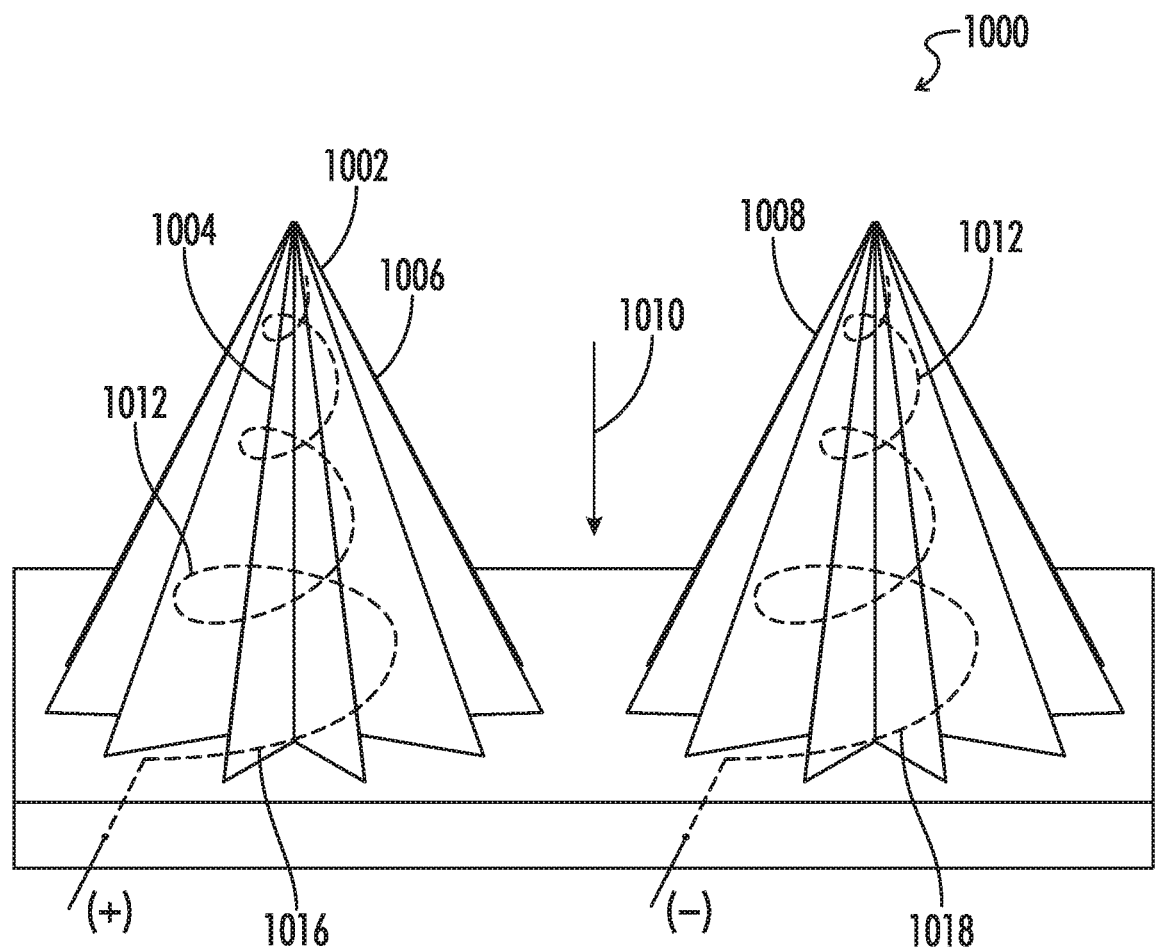
FIG. 10 is an embodiment of a spiral field effect electro-microstructured device.

Referring now to FIG. 10, a spiral field effect electro-microstructure device 1000 is illustrated. In some embodiments, such spiral structures may be useful in rapidly reversing the hydrophilic/hydrophobic state of devices. Device 1000 may be comprised of conical pillars 1002 with ridges 1004 on the pillar's outer wall. In one embodiment, two conical pillars 1006, 1008 may be adjacent to one another and wherein, between them is generated a rising surface energy in a downward direction 1010. This rising surface energy may generate a capillary force in said downward direction 1010. In some embodiments, the conical pillar 1002 may have an interior in which is disposed an electrode 1012. In one embodiment, the electrode 1012 may be arranged in a spiral configuration. The spiral configuration may be uniform, or the spiral configuration may taper outward as the diameter of the conical pillar 1002 increases. When the electrode 1012 is unpowered, the surface may be Wenzel wetting. When the electrode 1012 is powered, in embodiments where the electrode tapers outward, the field intensity increases as the electrode becomes more tightly wound toward the peak of the conical pillar 1002. When two adjacent conical pillars 1006, 1008 with tapered electrodes 1016, 1018 have opposing charges, then the surface energy gradient may be reversed in comparison to the uncharged state, resulting in a Cassie wetting state.

Figure 11:
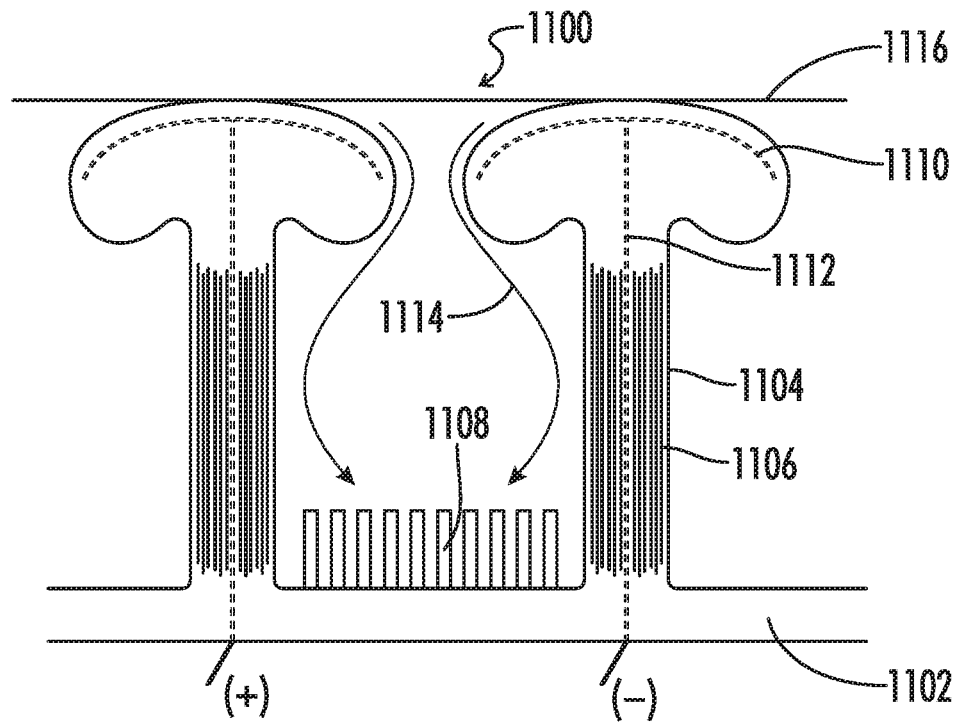
FIG. 11 is an embodiment of an electroadhesive microstructured device for wet conductive surfaces.

Example 8. An Electroadhesive Microstructured Device for Wet Conductive Surfaces Referring now to FIG. 11, an electro-microstructure device 1100 for adhesion to wet conductive surfaces is illustrated. Device 1100 may include a substrate layer 1102, first pillars 1104 with ridges 1106, second pillars 1108, electrodes 1110, and conductors 1112. In some embodiments, the substrate material may be hydrophilic and naturally wetting. The device 1100 may be configured such that when the device contacts a wet conductive surface, the water may be quickly wicked away as shown by the arrows 1114. When the water is quickly wicked away, the electrodes 1110 may come in close proximity to conductive surface 1116, which may greatly enhance the electroadhesion of the device 1100.

Figure 12:
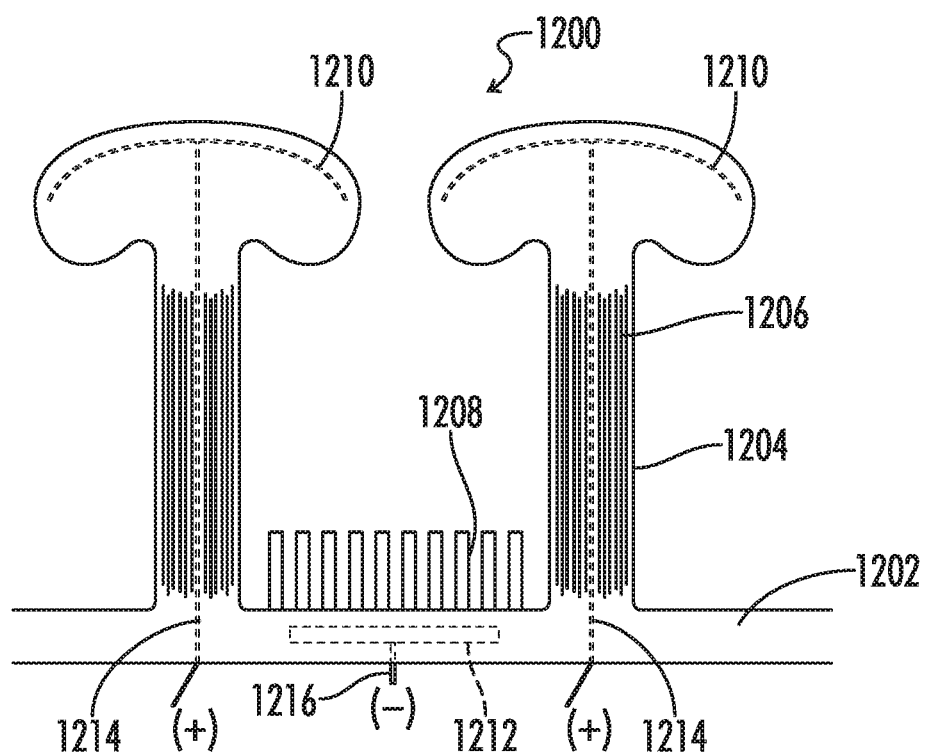
FIG. 12 is an embodiment of an electroadhesive microstructured device for nonconductive surfaces.

Example 9. An Electro Adhesive Microstructured Device for Nonconductive Surfaces Referring now to FIG. 12, an electro-microstructured device 1200 for adhesion to a wet non-conductive surface is illustrated. Device 1200 may include a substrate layer 1202, first pillars 1204 with ridges 1206, second pillars 1208, electrodes 1210, 1212, and conductors 1214, 1216. In some embodiments, the substrate material may be hydrophilic and naturally wetting. The device 1200 may be configured such that when the device contacts a wet nonconductive surface the water may be quickly wicked away. When the water is quickly wicked away, the electrodes 1210 may come into close proximity in a monopolar configuration.

Thus, although there have been described particular embodiments of the present disclosure of a new and useful Microstructured Field Effect Devices, it is not intended that such references be construed as limitations upon the scope of this disclosure except as set forth in the following claims.

What is claimed is:

1. An electro-microstructured device comprising:
a substrate having a hierarchical microstructure disposed thereon, the substrate having a thickness;
the hierarchical microstructure having a first microfeature, the first microfeature having a surface wherein a plurality of second microfeatures are disposed about the surface of the first microfeature; and
a first electrode and a second electrode, the first electrode and second electrode at least partially embedded within the thickness of the substrate and connected to a charge source, wherein the first electrode is configured to provide a positive charge of about +0.5V and the second electrode is configured to provide a negative charge of about −0.5V when powered by the charge source, and wherein charging the first electrode and second electrode generates an electroadhesive state via Wenzel-Cassie wetting domains.

2. The electro-microstructured device of claim 1, wherein the first electrode is configured to provide a local positive charge generating an electric field on a micrometer scale.

3. The electro-microstructured device of claim 1, wherein the first and second electrodes are adjacent to each other.

4. The electro-microstructured device of claim 1 wherein the substrate is a dielectric.

5. The electro-microstructured device of claim 3 wherein the space between the adjacent first and second electrodes includes an electric insulator.

6. The electro-microstructured device of claim 1 wherein the first and second electrodes further comprise a plurality of electrodes at least partially embedded within the thickness of the substrate which are arranged in an alternating positive charge and negative charge pattern.

7. The electro-microstructured device of claim 1 wherein the first microfeature has a height of 100 microns or less and a diameter of 20 microns or less.

8. The electro-microstructured device of claim 1 wherein the plurality of second microfeatures have a height of 5 microns or less and a diameter of 2 microns or less.

9. The electro-microstructured device of claim 1, wherein the substrate further comprises at least a portion that is hydrophobic, and wherein the first and second electrodes are arranged with the hierarchical microstructure to alter the substrate portion that is hydrophobic to a portion that is hydrophilic when the electrodes are charged.

10. The electro-micro structured device of claim 1, wherein the substrate further comprises at least a portion that is hydrophilic, and wherein the first and second electrodes are arranged with the hierarchical microstructures to alter the substrate portion that is hydrophilic to a portion that is hydrophobic when the electrodes are charged.

11. The electro-microstructured device of claim 1, wherein at least a portion of the first electrode is disposed within the first microfeature.

12. The electro-microstructured device of claim 1, wherein at least a portion of the first electrode is disposed within the second microfeature.

13. An electro-microstructured device comprising:
a substrate having a thickness, and including a hierarchical microstructure disposed thereon, wherein the hierarchical microstructure includes a layer of metallic particulates disposed thereon,
the hierarchical microstructure having a first microfeature, the first microfeature having a surface wherein a plurality of second microfeatures are disposed about the surface of the first microfeature; and
a first electrode and a second electrode, the first electrode and second electrode at least partially embedded within the thickness of the substrate and connected to a charge source, wherein the first electrode is configured to provide a positive charge of about +0.5V and the second electrode is configured to provide a negative charge of about −0.5V when powered by the charge source, and wherein charging the first electrode and second electrode generates an electroadhesive state via Wenzel-Cassie wetting domains.

14. The electro-microstructured device of claim 13 wherein the first microfeature has a height of 100 microns or less and a diameter of 20 microns or less.

15. The electro-microstructured device of claim 13 wherein the plurality of second microfeatures have a height of 5 microns or less and a diameter of 2 microns or less.

16. The electro-microstructured device of claim 13 wherein the metallic particulates have a diameter ranging between 0.1 to 1.0 microns.

17. The electro-microstructured device of claim 13 wherein the hierarchical microstructure further includes two distinct microstructure regions, a first region wherein the metallic particulates comprise zinc, and a second region wherein the metallic particulates comprise silver.

18. The electro-microstructured device of claim 13 wherein the hierarchical microstructure further includes two distinct microstructure regions, a first region wherein the metallic particulates comprise zinc, and a second region wherein the metallic particulates comprise gold.

* * * * *